United States Patent [19]

Urban, Jr. et al.

[11] Patent Number: 4,874,605
[45] Date of Patent: Oct. 17, 1989

[54] STABILIZED DELAYED RELEASE EMULSION

[75] Inventors: Joseph J. Urban, Jr., Richboro, Pa.; Norman Henderson, Gladstone, N.J.; Anthony J. Behe, Harleysville, Pa.

[73] Assignee: Hoechst-Roussel Pharmaceuticals Inc., Somerville, N.J.

[21] Appl. No.: 125,673

[22] Filed: Nov. 27, 1987

[51] Int. Cl.$^4$ ............................................. A61K 31/74
[52] U.S. Cl. ...................................... 424/78; 514/941; 514/943; 514/938; 514/944
[58] Field of Search ............... 514/941, 943, 938, 944; 424/78

[56] References Cited

U.S. PATENT DOCUMENTS

| Re. 32,393 | 4/1987 | Wretlind et al. | 514/943 X |
|---|---|---|---|
| 3,085,939 | 4/1963 | Wruble et al. | 514/938 X |
| 3,640,741 | 2/1972 | Etes | 514/944 X |
| 3,939,260 | 2/1976 | Lafon | 252/91 X |
| 4,379,755 | 4/1983 | Yamada et al. | 514/943 X |
| 4,542,011 | 9/1985 | Gleixner | 424/470 X |

FOREIGN PATENT DOCUMENTS

| 2057957 | 5/1971 | Fed. Rep. of Germany | 514/943 |
|---|---|---|---|
| 58-027636 | 2/1983 | Japan | 514/943 |

Primary Examiner—Thurman K. Page
Attorney, Agent, or Firm—Raymond Wittekind

[57] ABSTRACT

A stabilized delayed release emulsion comprising:
(a) a lipophilic external phase, and
(b) a hydrophilic phase having incorporated therein:
  (i) a pharmaceutically active ingredient, said pharmaceutically active ingredient being substantially insoluble in said lipophilic phase; and
  (ii) a gelling agent; and
a process for preparing same are disclosed.

10 Claims, 1 Drawing Sheet

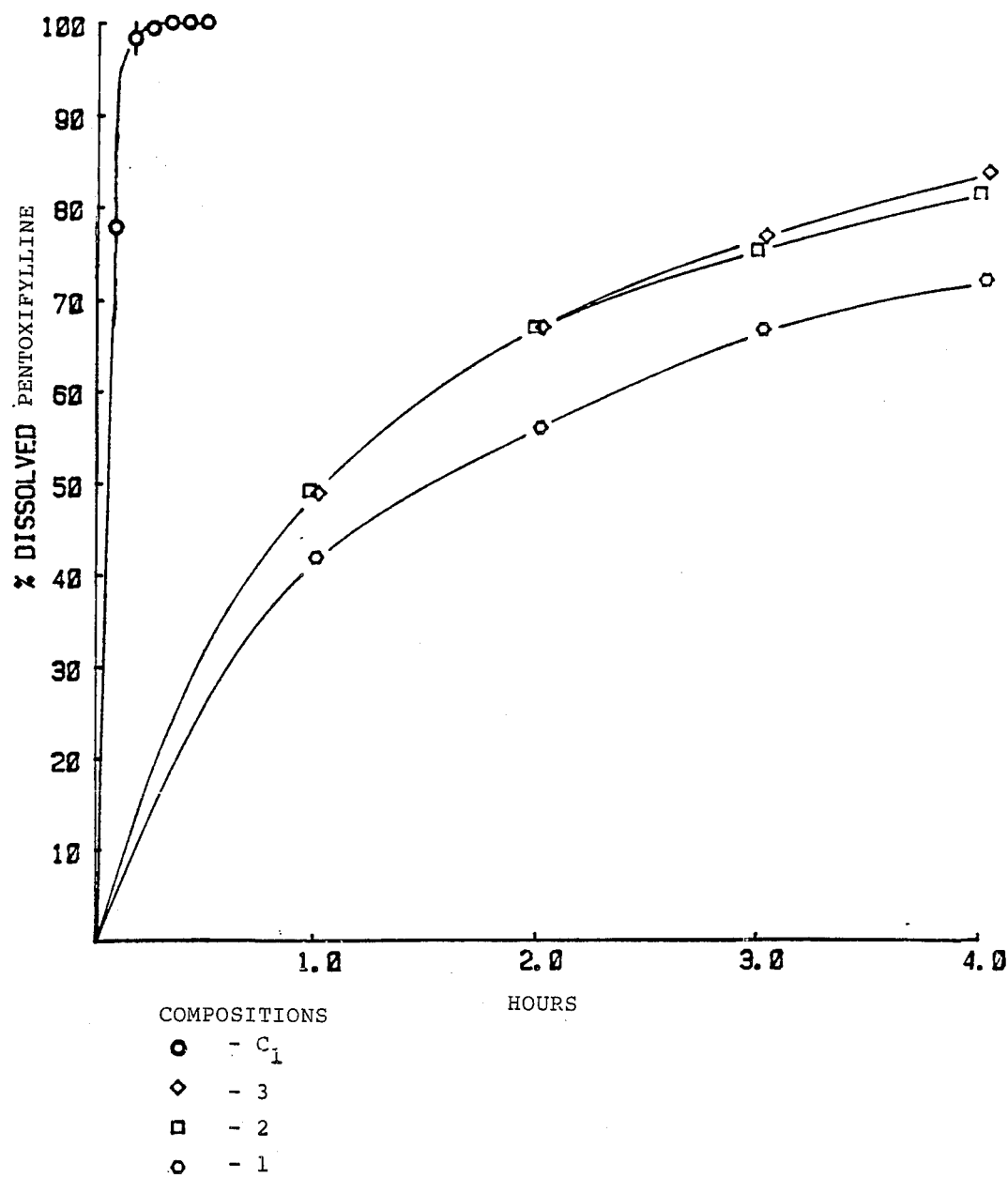

STABILIZED DELAYED RELEASE EMULSION

This invention relates to a stabilized delayed release emulsion suitable for the oral administration of a pharmaceutically active ingredient and to a process for preparing same.

BACKGROUND OF THE INVENTION

Owing to their ability to be relatively easily formulated, manufactured, handled and stored, tablets and capsules are the oral administration means of choice for a majority of drug products. Troches, syrups, suspensions, and gums are alternative administration means to tablets or capsules. Although drugs are generally more easily ingested via these alternative administration means by users having difficulty swallowing tablets or capsules, such compositions are generally unable to provide the delayed release properties obtainable with tablet and capsule formulations. Further, despite the use of flavoring additives, the above described alternative administration means are oftentimes unable to mask the bitter or otherwise objectionable taste or aftertaste of many medicaments. Additionally, suspensions and syrups are prone to problems such as sedimentation and/or crystallization.

Emulsified systems represent a class of oral administration means which have been effectively used to mask objectionable tasting medicaments. Currently marketed emulsions include oil-in-water type systems formulated as vitamin supplements and laxatives. Oil-in-water type systems tend to break down at relatively rapid rates following ingestion and are generally unsuitable for those applications wherein the delayed release of a pharmaceutically active ingredient is required. Further, the utility of such state of the art emulsions has been limited by their tendency to separate, with the passage of time, into distinct oil and water phases.

It is an object of this invention to provide an easily ingestible drug administration means having delayed release properties. It is a further object of this invention to provide an oral administration means capable of masking bitter or objectionable testing medicaments. It is yet another object of this invention to provide a physically stable oral administration means.

SUMMARY OF THE INVENTION

In one embodiment this invention relates to a stabilized delayed release emulsion comprising:
(a) a lipophilic external phase,
(b) a hydrophilic internal phase having incorporated therein:
 (i) a pharmaceutically active ingredient, said pharmaceutically active ingredient being substantially insoluble in said external phase, and
 (ii) a gelling agent.

Preferably, the emulsions of this invention are formulated to release less than 75 weight percent, preferably less than about 50 weight percent, of active ingredient within 1 hour of administration.

BRIEF DISCUSSION OF FIGURE

The FIGURE shows the percent dissolution of pentoxifylline as a function of time.

In a further embodiment, this invention relates to a process for preparing a stabilized delayed release emulsion which comprises the steps of:

(a) forming a base by combining a lipophilic phase with a hydrophilic phase having incorporated therein:
 (i) a pharmaceutically active ingredient, said pharmaceutically active ingredient being substantially insoluble in said lipophilic phase; and
 (ii) a gelling agent;
(b) liquifying the base;
(c) subjecting the base to a shear force to emulsify the hydrophilic and lipophilic phases; and
(d) cooling the emulsified base to a temperature at which gelling is effected.

The emulsions of this invention ordinarily exist as paste-like solids at temperatures to about 40° C. However, normally liquid systems (i.e. emulsions which exist in liquid form at temperatures of about 20° C.) are also within the scope of this invention. The physical state of a given emulsion will depend in large part on the selection of the hydrophilic and lipophilic phase media, and the relative amounts thereof.

The internal phase of the emulsion of this invention comprises a non-toxic, hydrophilic medium. Among the materials suitable for use as a hydrophilic phase medium there may be mentioned, for example, water, glycerin, propylene glycol, polyethylene glycols, and mixtures thereof. For purposes of this invention, water is the preferred hydrophilic medium.

The external phase of the emulsion of this invention comprises a non-toxic, lipophilic medium. Among the materials suitable for use as the lipophilic medium of this invention there may be mentioned, for example, saturated and unsaturated fatty acids and alcohols, the mono-, di, and tri-ester derivatives thereof, and mixtures thereof. Exemplary of such lipophilic media are oils of animal and vegetable origin, for example, lard, peanut, sesame, rapeseed, cottonseed, corn, sunflower, sassafras, safflower, coconut and olive oils; and ethylene oxide/propylene oxide copolymers. Unsaturated vegetable oils are the preferred lipophilic phase medium.

For purposes of this invention it is required that the pharmaceutically active ingredient be substantially insoluble in the lipophilic phase. "Substantially insoluble" is herein defined as having a solubility of less than about 3.0 weight percent at 20° C.

In general, the emulsions of this invention comprise from about 20 to about 60, preferably from about 25 to about 35, percent by weight, based on the total weight of the emulsion, of a hydrophilic phase, and from about 80 to about 40, preferably from about 75 to about 65, percent by weight, based on the total weight of the emulsion, of a lipophilic phase.

Gelling agents suitable for use in the internal phase of this invention are those compositions capable of increasing the viscosity of the resulting emulsion. Suitable gelling agents include cellulose derivatives such as carboxymethyl cellulose, cellulose acetate, methyl cellulose, hydroxyethyl cellulose, hydroxypropyl cellulose and the like; natural gums such as gum arabic; xanthum gum, karage, tragacanth gum, guar gum and the like; gelatin; silicon dioxide; synthetic polymers such as carbomers, polyvinylpyrrolidine, polyvinylacetate, polyvinylalcohol, and the like; and mixtures thereof. Gelatin, and modified celluloses represent a preferred class of gelling agents. If desired, the gelling agents may also be present in the lipophilic phase of the instant emulsion. In general, the amount of gelling agent present in the emulsion of this invention ranges from about 0.01 to about 5 percent, preferably from about 0.1 to about 2 percent, of the total weight thereof.

In addition to the above described components, the emulsion of this invention may further comprise one or more of the following optional additives: antioxidants such as, for example, ascorbyl palmitate, sodium bisulfite, sodium metabisulfite, and the like; and mixtures thereof. Preservatives such as, for example, potassium sorbate, sodium benzoate, sorbic acid, propyl gallate, and the like; sequestering agents (e.g. ethylenediaminetetraacetic acid), flavoring agents (e.g. natural vanillin) coloring agents, buffers (e.g. citric acid), densification agents (e.g. magnesium salts), emulsifiers (e.g. glycerol monostearate) and the like, and mixtures thereof. When present, the total amount of such additional additives typically does not exceed about 25% of the total weight of the emulsion. The optional additives may be present in either or both of the emulsion phases.

The emulsions of this invention may be prepared by subjecting a base comprising a combination of
(a) liopophilic phase, and
(b) a hydrophilic phase having incorporated therein:
  (i) a pharmaceutically active ingredient, said pharmaceutically active ingredient being substantially insoluble in the lipophilic phase, and
  (ii) a gelling agent to a temperature sufficient to liquify same, typically from about 40° C. to about 80° C., applying a shear force sufficient to emulsify the hydrophilic and lipophilic phases of the base, and cooling the emulsified base of a temperature at which gelling is effected (e.g. 20° C. to 30° C.). If desired, liquefaction of the base may be accomplished simultaneously with emulsification. Emulsification may be accomplished by any of several methods which include agitation, mixing, milling and homogenation. Prior or subsequent to cooling, the emulsified system may be incorporated into a suitable dispensing means (i.e., bottles, jars, tubes, etc.).

Additional optional ingredients may be incorporated into the lipophilic and/or hydrophilic phases of the system prior to the formation of the base. Alternatively, the additional optional ingredients may be incorporated into the formed base prior to emulsification.

EXAMPLES

The following examples serve to illustrate specific embodiments of this invention. It is not intended that the scope of the invention shall be limited by these examples. All precentages provided in the examples which follow are by weight.

EXAMPLES 1 TO 3 AND COMPARATIVE EXAMPLE 1

Compositions prepared according to the specifications of Table 1 were prepared by means of the following procedure:

(1) partially hydrogenated vegetable oil and glycerol monostearate components are combined and heated to about 80° C.;
(2) gelatin, potassium sorbate, vanillin and pentoxifylline components are dissolved in the purified water component and heated to 60° C.;
(3) after cooling to 60° C. the mixture prepared in step (1) is combined with the mixture of step (2) and homogenized in a high shear blender; and
(4) upon cooling to below about 40° C. the homogenate of step (3) is treated with the sorbic acid component, subjected to high shear, and then cooled to room temperature.

TABLE 1

| Component | 1 | 2 | 3 | C |
|---|---|---|---|---|
| Partially hydrogenated vegetable oil | 62.0% | 55.0% | 45.0% | 0% |
| Gycerol monostearate SE | 5.0% | 5.0% | 5.0% | 0% |
| Sorbic Acid | 0.1% | 0.1% | 0.1% | 0% |
| Purified water VSP | 29.2% | 36.2% | 46.2% | 96.7% |
| Gelatin | 0.1% | 0.1% | 0.1% | 0% |
| Potassium sorbate | 0.1% | 0.1% | 0.1% | 0% |
| Vanilin | 0.2% | 0.2% | 0.2% | 0% |
| Pentoxifylline | 3.3% | 3.3% | 3.3% | 3.3% |

Compositions 1, 2, 3 and $C_1$ were subjected to dissolution testing using the procedure and apparatus (Apparatus 2) described in *The United States Pharmacopeia Twentieth Revision* 1980/*The National Formulary Fifteenth Edition* 1980, at p. 959.

The apparatus utilized in this procedure is a 100 ml cylindrical glass vessel 16.0-17.5 cm high having an inside diameter of 10.0 to 10.5 cm, and a spherical bottom. The vessel is equipped with a variable speed drive, a heating means and a stirring element. The stirring element is a metal shaft 10±0.5 mm in diameter, positioned in the cylinder in alignment with the vertical axis thereof. Extending through the bottom of the shaft is a blade, the bottom of which is flush with the shaft bottom. The blade is 3.0 to 5.0 mm thick and forms a section of a circle 83 mm in diameter, and is subtended by parallel chords of 42±1 mm and 75±1 mm. The blade is positioned horizontally at the end of the shaft so that the 42 mm edge is nearest the bottom inner surface of the vessel, and a distance of 2.5±0.2 cm between the blade and bottom inner surface is maintained.

The dissolution test procedure employed in this series of Examples utilizes, as a dissolution medium, simulated gastric fluid prepared by the dissolution of 2.0 g of sodium chloride in 7.0 ml of hydrochloric acid and sufficient water to make 1000 ml of solution. The simulated gastric fluid (900 ml) is introduced to the dissolution apparatus and heated to a temperature of 37±0.5° C., which temperature is maintained for the duration of the test. A 7.5 g sample of the composition of interest is introduced to the dissolution apparatus and the variable speed drive is activated to maintain a blade speed of 100 revolutions per minute. At one hour intervals a 5 cc sample of the dissolution medium is withdrawn and analyzed to determine the amount of pharmacologically active ingredient (pentoxifylline) released into same.

The results of the dissolution test procedure for the compositions of Examples 1, 2, 3 and $C_1$ is depicted graphically in the FIGURE which follows. As illustrated, emulsions formulated to the specifications of Examples 1, 2 and 3 provide delayed release properties unobtainable with a solution $C_1$.

What is claimed is:
1. An emulsion comprising:
(a) a lipophilic external phase,
(b) a hydrophilic internal phase having incorporated therein:
  (i) pentoxifylline, said pentoxifylline being substantially insoluble in the lipophilic external phase; and
  (ii) a gelling agent.
2. An emulsion as defined in claim 1 wherein the hydrophilic phase comprises a medium selected from the group consisting of water, glycerin, propylene glycol, polyethylene glycols, and mixtures thereof.
3. An emulsion as defined in claim 2 wherein the lipophilic phase comprises a medium selected from the group consisting of saturated and unsaturated fatty acids and alcohols, the mono-, di- and tri-ester derivatives thereof, and mixtures thereof.

4. An emulsion as defined in claim 3 wherein the gelling agent is selected from the group consisting of gelatin, guar gum, acacia, silicon dioxide, carbon vinyl polymers, cellulose derivatives, and the like, and mixtures thereof.

5. An emulsion as defined in claim 4 wherein the lipophilic external phase comprises from about 65 to about 75 weight percent of the total weight of the emulsion and the hydrophilic internal phase comprises from about 35 to about 25 percent of the total weight of the emulsion.

6. An emulsion as defined in claim 5 wherein the hydrophilic phase medium is water; the lipophilic phase medium comprises one or more vegetable oils; and the gelling agent is gelatin.

7. An emulsion as defined in claim 6 wherein the gelling agent comprises from about 0.1 to about 2.0 percent by weight of the total weight of the emulsion.

8. An emulsion as defined in claim 5 which further comprises at least one optional additive selected from the group consisting of preservatives, sequestering agents, flavoring agents, coloring agents, buffers, densification agents and emulsifiers.

9. An emulsion as defined in claim 8 wherein the preservative is a combination of potassium sorbate and sorbic acid, and the emulsifier is glycerol monostearate.

10. An emulsion as defined in claim 5 wherein the pharmaceutically active ingredient has a solubility in the lipophilic external phases of less than 3.0 weight percent at 20° C.

* * * * *